(12) United States Patent
Sherman

(10) Patent No.: US 10,859,565 B2
(45) Date of Patent: Dec. 8, 2020

(54) HIGH THROUGHPUT 3D ASSAY FOR IMMUNE CELL AND DRUG HOMING, MIGRATION AND TUMOR CYTOTOXICITY

(71) Applicant: Corning Incorporated, Corning, NY (US)

(72) Inventor: Hilary A. Sherman, Madbury, NH (US)

(73) Assignee: Corning Incorporated, Corning, NY (US)

( * ) Notice: Subject to any disclaimer, the term of this patent is extended or adjusted under 35 U.S.C. 154(b) by 264 days.

(21) Appl. No.: 15/889,766

(22) Filed: Feb. 6, 2018

(65) Prior Publication Data

US 2018/0224428 A1 Aug. 9, 2018

Related U.S. Application Data

(60) Provisional application No. 62/455,881, filed on Feb. 7, 2017.

(51) Int. Cl.
*G01N 33/50* (2006.01)
*C12N 5/09* (2010.01)

(52) U.S. Cl.
CPC ....... *G01N 33/5011* (2013.01); *C12N 5/0693* (2013.01); *G01N 33/5014* (2013.01); *G01N 33/5029* (2013.01); *G01N 33/5044* (2013.01); *G01N 33/5088* (2013.01); *C12N 2501/02* (2013.01); *C12N 2501/21* (2013.01); *C12N 2502/28* (2013.01); *C12N 2503/02* (2013.01); *C12N 2513/00* (2013.01); *G01N 2500/10* (2013.01)

(58) Field of Classification Search
CPC .......... G01N 33/5011; G01N 33/5044; G01N 33/5014; G01N 2500/10; C12N 5/0693; C12N 2513/00; C12N 2503/02; C12N 2502/28
See application file for complete search history.

(56) References Cited

FOREIGN PATENT DOCUMENTS

WO 2016069917 A1 5/2016

OTHER PUBLICATIONS

Katt et al., In vitro tumor models: Advantages, disadvantages, variables, and selecting the right platform. Frontiers in Bioengineering and Biotechnology, vol. 4. No. 12 (Feb. 12, 2016) pp. 1-14., (Year: 2016).*

(Continued)

*Primary Examiner* — Kara D Johnson
(74) *Attorney, Agent, or Firm* — Annie J. Kock

(57) ABSTRACT

The present disclosure relates to methods for performing assays for active migration and cytotoxicity of a therapeutic agent towards tumor cells, e.g., immune cell and/or drug homing, migration, and tumor cytotoxicity. The methods are performed in labware that provide opportunities for a therapeutic agent, such as an immune cell or a drug, to migrate toward tumor cells, including tumor cells growing in a 3D spheroid conformation. The methods allow for, among other uses, the investigation of the effects of a therapeutic agent, such as immune cells or a drug, on tumor cells, and enable the investigation of homing, tumor cytotoxicity, and tumor immune evasion in a single, easy-to-use, high throughput system for more in vivo-like testing.

18 Claims, 14 Drawing Sheets

(56) References Cited

OTHER PUBLICATIONS

Patra et al., Drug testing and flow cytometry analysis on a large number of uniform sized tumor spheroids using a microfluidic device, Scientific Reports, vol. 6 (Feb. 15, 2016) pp. 1-12. (Year: 2016).*

Achilli et al; "Advances in the Formation, Use and Understanding of Multi-Cellular Spheroids"; Expert Opin Biol Ther.; 12 (10), (2012) pp. 1347-1360.

Berahovich et al; "Evidence for NK Cell Subsets Based on Chemokine Receptor Expression"; J Immunol 2006; 177: 7833-7840.

Dangles-Marie et al; "A Three-Dimensional Tumor Cell Defect in Activating Autologous CTLS is Associated With Inefficient Antigen Presentation Correlated With Heat Shock Protein-70 Down-Regulation"; Cancer Research 63, pp. 3682-3687, July 1, 2003.

Herter et al; "A Novel Three-Dimensional Heterotypic Shperoid Model for the Assessment of the Activity of Cancer Immunotherapy Agents"; Cancer Immunol. Immunother (2017) 66: 129-140.

Holmes et al; "A Human NK Cell Activation/Inhibition Threshold Allows Small Changes in the Target Cell Surface Phenotype to Dramatically Alter Susceptibility to NK Cells"; J. Immunol 2011; 186; 1538-1545; 2010.

Holt et al; "Prostaglandin E2 (PGE2) Suppresses Natural Killer Cell Function Primarily Through the PGE2 Receptor EP4"; Cancer Immunol Immunother, Nov. 2011, 60 (11); pp. 1577-1586.

Huang et al; "SCF-Mediated Mast Cell Infiltration and Activation Exaverbate the Inflammation and Immunosuppression in Tumor Microenvironment"; Blood, (2008) vol. 112, No. 4; pp. 1269-1279.

Koeck et al; "Infiltration of Lymphocyte Subpopulations Into Cancer Microtissues as a Tool for the Exploration of Immunomodulatory Agents and Biomarkers"; Immunobiology; 221 (2016) pp. 604-617.

International Search Report and Written Opinion PCT/US2018/017081 dated May 8, 2018.

Akasov et al. "ultrasonically assisted polysaccharide microcontainers for delivery of lipophilic antitumor drugs: preparation and in vitro evaluation", ACS Applied Materials & Interfaces, 7(30) 2015, pp. 16581-16589.

Singh et al. "Cytotoxicity of curcumin silica nanoparticle complexes conjugated with hyaluronic acid on colon cancer cells", International Journal of Biological Macromolecules, 74, 2015, pp. 162-170.

Ma et al. "Vincristine liposomes with smaller particle size having stronger diffusion ability in tumor and improve tumor accumulation of vincristine significantly", Oncotarget, 8(50), 2017, pp. 87276-87291.

* cited by examiner

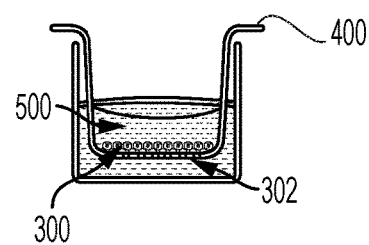
FIG. 8A
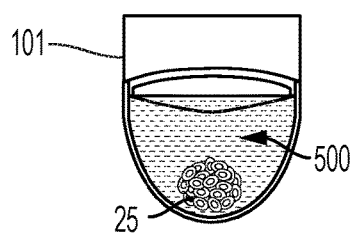
FIG. 8B
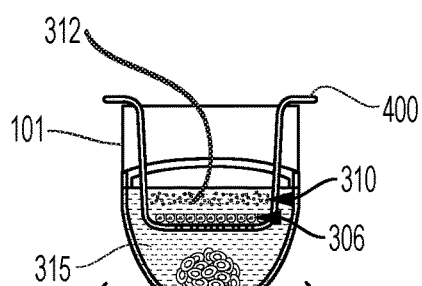
FIG. 8C
FIG. 8D 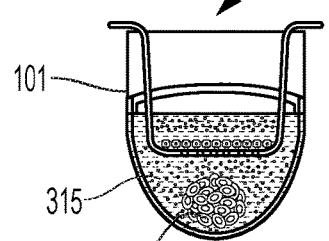 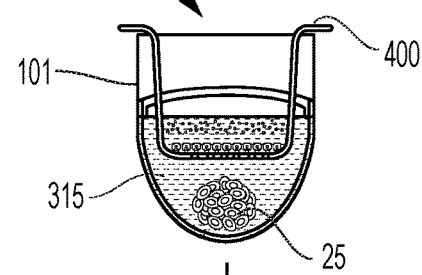 FIG. 8E
FIG. 8F 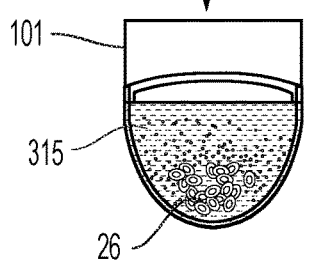 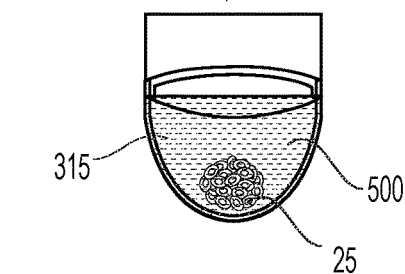 FIG. 8G

|   | 1 | 2 | 3 | 4 | 5 | 6 |
|---|---|---|---|---|---|---|
| A | BUFFER | 0414 AG 490 | 0431 ML 9 HYDROCHLORIDE | 3439 NH 125 | 0541 FASUDIL HYDROCHLORIDE | 0741 GF 109203X |
| B | BUFFER | 1264 SB 202190 | 1284 OLOMOUCINE | 1300 LFM-A 13 | 1321 ZM 336372 | 1366 ZM 449829 |
| C | BUFFER | 1407 PP 2 | 1459 SU 4312 | 1496 SP 600125 | 1580 PURVALANOL A | 1581 PURVALANOL B |
| D | BUFFER | 1937 NSC 693868 | 1962 SB 239063 | 1969 SL 327 | 2002 RO 31-8220 MESYLATE | 2072 AMINOPUR-VALANOL A |
| E | BUFFER | 2291 1,2,3,4,5,6-HEXABROMOCYCLOHEXANE | 2415 HA 1100 HYDROCHLORIDE | 2416 BIB X 1382 DIHYDROCHLORIDE | 2442 CGP 53353 | 2457 ARCYRIAFLAVIN A |
| F | BUFFER | 2542 Ki 8751 | 2558 10-DEBC HYDROCHLORIDE | 2559 TP CA-1 | 2560 SB 218078 | 2591 TCS 359 |
| G | BUFFER | 2694 PD 407824 | 2718 LY 364947 | 2731 CGP 57380 | 2768 PQ 401 | 2814 PI 828 |
| H | BUFFER | 2977 GW843682X | 3000 IRESSA | 3037 SU 5416 | 3063 1-NAPHTHYL PP1 | 3572 GSK 650394 |

FIG. 13A

|   | 7 | 8 | 9 | 10 | 11 | 12 |
|---|---|---|---|---|---|---|
| A | 1110 GENISTEIN | 1130 LY 294002 HYDROCHLORIDE | 1144 U0126 | 1213 PD 98059 | 1254 Y-27632 DIHYDROCHLORIDE | BUFFER |
| B | 1367 ZM 39923 HYDROCHLORIDE | 1381 GW 5074 | 1397 PP 1 | 1402 SB 203580 HYDROCHLORIDE | 1405 (-)-TERREIC ACID | BUFFER |
| C | 3544 KU 55933 | 1614 SB 431542 | 1616 SB 216763 | 1617 SB 415286 | 1777 ARCTIGENIN | BUFFER |
| D | 2151 API-2 | 2238 GW 441756 | 2239 GW583340 DIHYDROCHLORIDE | 2272 Ro 08-2750 | 2275 TBB | BUFFER |
| E | 2458 ZM 447439 | 2471 ER 273 19 MALEATE | 2475 ZM 323881 HYDROCHLORIDE | 2499 ZM 306416 HYDROCHLORIDE | 2539 IKK 16 | BUFFER |
| F | 2605 P D 198306 | 2609 RYUVIDINE | 2611 IM D 0354 | 2639 CGK 733 | 2693 PHA 665752 | BUFFER |
| G | 2828 NU 7026 | 2902 D 4476 | 2908 EO 1428 | 2910 H 89 DIHYDROCHLORIDE | 2926 FPA 124 | BUFFER |
| H | 3194 BIO | 3269 SD 208 | 3271 COMPOUND 401 | 3314 BI 78D3 | 3318 SC 514 | BUFFER |

FIG. 13B

HIGH THROUGHPUT 3D ASSAY FOR IMMUNE CELL AND DRUG HOMING, MIGRATION AND TUMOR CYTOTOXICITY

CROSS-REFERENCE TO RELATED APPLICATIONS

This application depends from and claims priority to U.S. Provisional Application No. 62/455,881 filed on Feb. 7, 2017, the entire contents of which are incorporated herein by reference.

FIELD

The present disclosure generally relates to methods for performing assays for active migration and cytotoxicity of a therapeutic agent towards tumor cells, e.g., immune cell and/or drug homing, migration, and tumor cytotoxicity. The methods are performed in labware that provide opportunities for a therapeutic agent, such as an immune cell or a drug, to migrate toward tumor cells, including tumor cells growing in a 3D spheroid conformation. The methods allow for, among other uses, the investigation of the effects of a therapeutic agent, such as immune cells or a drug, on tumor cells, and enable the investigation of homing, tumor cytotoxicity, and tumor immune evasion in a single, easy-to-use, high throughput system for more in vivo-like testing.

TECHNICAL BACKGROUND

Traditionally, in vitro models investigating the homing and tumoricidal activity of a therapeutic agent and the immune evasion of a tumor have been studied independently by utilizing two dimensional systems (2D) of tumor cells, which may not accurately reflect the complexity of a three dimensional (3D) tumor, or by studying cytotoxicity with a 3D tumor cell model, but without the migration component. Importantly, the barriers immune cells and drugs need to overcome in a 3D tumor cell system are much greater than those of 2D tumor cell system. For example, immune cells not only need to migrate to the tumor site, but also need to infiltrate the 3D tumor structure in order to attack the target tumor cells. Beyond the physical differences between a 2D and 3D system, it has been shown that phenotypic differences also occur when tumor cells are cultured in 3D, with these phenotypic differences allowing for higher resistance to cytotoxicity. Therefore, although there has been increasing interest in utilizing immune cells for cancer treatment, with therapy involving activating a patient's own immune cells (e.g., T cells, NK cells, B cells, etc.) to attack their tumors, the effectiveness of immunotherapy is not equivalent for all patients or cancer types, which has led to the need for better models for scientists and researchers.

Accordingly, on-going need exists for alternative models and methods to enable the investigation immune cell and drug homing, tumor cytotoxicity, and tumor immune evasion in a single, easy-to-use, high throughput system for more in vivo-like testing.

SUMMARY OF THE DISCLOSURE

In accordance with various embodiments of the present disclosure, methods and labware for assaying therapeutic agents, including immune cells and drugs, and their effects on tumor cells growing in 3D spheroid conformation in culture are disclosed herein. The methods allow for, among other uses, the investigation of the effects of a therapeutic agent, such as immune cells or a drug, on tumor cells, and enable the investigation of homing, tumor cytotoxicity, and tumor immune evasion in a single, easy-to-use, high throughput system for more in vivo-like testing.

In various embodiments, an assay method for detecting active migration and cytotoxicity of a therapeutic agent is disclosed. The assay method includes culturing tumor cells in a cell culture article to form a spheroid, wherein the cell culture article comprises a chamber structured to constrain the tumor cells to grow in a 3D spheroid conformation. The assay method further includes placing an insert comprising a porous membrane into the cell culture article and introducing a therapeutic agent into the insert. The assay method also includes detecting active migration of the therapeutic agent from the insert into the cell culture article chamber and detecting tumor cell response. In embodiments, tumor cell response may be tumor cell lysis, infiltration of the therapeutic agent into the tumor cell spheroid, or measurements of changes in tumor cell physiology.

In some embodiments, both active migration of the therapeutic agent and tumor cell lysis are detected by flow cytometry. In some embodiments, the assay method further includes detecting infiltration of the therapeutic agent, such an immune cell, into the tumor cell spheroid.

In some embodiments, the therapeutic agent is a cell therapeutic and/or a drug. In some embodiments, the cell therapeutic includes an immune cell. In some embodiments, the immune cell is a leukocyte. In some embodiments, the immune cell is a lymphocyte.

In some embodiments of an assay method for detecting active migration and cytotoxicity of a therapeutic agent, the chamber of the cell culture article includes a side wall, a top aperture, and a liquid impermeable bottom comprising at least one concave surface. In embodiments, at least a portion of the bottom surface includes a low-adhesion or no-adhesion material in or on the at least one concave surface. In some embodiments, the liquid impermeable bottom including at least one concave surface is gas-permeable. In some embodiments, the side wall is opaque. In some embodiments, at least a portion of the bottom is transparent.

In some embodiments of an assay method for detecting active migration and cytotoxicity of a therapeutic agent, the cell culture article includes from 1 to about 2,000 of said chambers, wherein each chamber is physically separated from any other chamber. In some embodiments, the at least one concave surface of the chamber includes a plurality of concave surfaces within the same chamber.

In some embodiments of an assay method for detecting active migration and cytotoxicity of a therapeutic agent, the at least one concave surface the chamber of the cell culture article includes a hemi-spherical surface, a conical surface having a taper of 30 to about 60 degrees from the side walls to the bottom surface, or a combination thereof.

In some embodiments of an assay method for detecting active migration and cytotoxicity of a therapeutic agent, the side wall surface of the chamber of the cell culture article includes a vertical cylinder, a portion of a vertical conic of decreasing diameter from the chamber's top to bottom surface, a vertical square shaft having a conical transition to the at least one concave bottom surface, or a combination thereof.

In some embodiments of an assay method for detecting active migration and cytotoxicity of a therapeutic agent, the cell culture article further includes a chamber annex for receiving a pipette tip for aspiration, the chamber annex including a surface adjacent to and in fluid communication with the chamber, the chamber annex having a second bottom spaced away and at an elevation above the bottom surface, wherein the second bottom deflects fluid dispensed rom a pipette away from the bottom surface.

In some embodiments of an assay method for detecting active migration and cytotoxicity of a therapeutic agent, the insert includes an insert plate.

In some embodiments of an assay method for detecting active migration and cytotoxicity of a therapeutic agent, at least a portion of the porous membrane is configured to simulate a biological barrier. In some embodiments, the biological barrier is a blood-brain barrier. In some embodiments, at least a portion of the porous membrane includes an essentially confluent monolayer of microvascular endothelial cells.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

DESCRIPTION OF THE FIGURES

The following detailed description of specific embodiments of the present disclosure can be best understood when read in conjunction with the following drawings, where like structure is indicated with like reference numerals and in which:

FIG. 1A shows a multi-well microplate. FIG. 1B shows illustrates a single well of the multi-well plate. FIG. 1C is an exploded view of the area of the bottom surface of the single well shown in the box C in FIG. 1B.

FIGS. 8A, 8B, 8C, 8D, 8E, 8F and 8G are illustrations of methods disclosed herein.

FIG. 13A and FIG. 13B are graphs of the screen summary of FIG. 12A and FIG. 12B showing the compilation of hits discovered with and without a BBB. Results were considered "hits" if they were 3 sigma below buffer response in at least 2 of 3 independent screens. Boxes with a horizontal hatching (besides buffer alone) are hits only found without BBB. Boxes with a diagonal hatching were hits found with and without BBB.

DETAILED DESCRIPTION

Figure 1A:
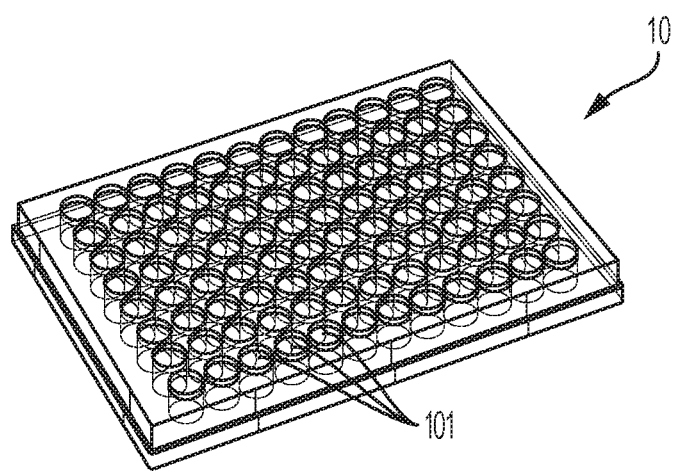
FIG. 1A, FIG. 1B and FIG. 1C show an embodiment of a multi-well microplate, in this case a 96-well spheroid microplate, having an array of microcavities on the bottom surface of each well to provide multiple spheroids in each of the 96 wells.

Reference will now be made in greater detail to various embodiments of the subject matter of the present disclosure, some embodiments of which are illustrated in the accompanying drawings. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Definitions

As used herein, singular forms "a," "an" and "the" include plural referents unless the context clearly dictates otherwise. Thus, for example, reference to a "structured bottom surface" includes examples having two or more such "structured bottom surfaces" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Also herein, the recitations of numerical ranges by endpoints include all numbers subsumed within that range (e.g., 1 to 5 includes 1, 1.5, 2, 2.75, 3, 3.80, 4, 5, etc.). It should be further understood that every numerical range given throughout this specification will include every narrower numerical range that falls within such broader numerical range, as if such narrower numerical ranges were all expressly written herein. Where a range of values is "greater than", "less than", etc. a particular value, that value is included within the range.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture apparatuses often refer to directions when the apparatus is oriented for purposes of culturing cells in the apparatus.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

As used herein, the term "cell culture" refers to keeping cells alive in vitro. Included within this term are continuous cell lines (e.g., with an immortal phenotype), primary cell cultures, finite cell lines (e.g., non-transformed cells), and any other cell population maintained in vitro, including oocytes and embryos.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "cell culture article" means any container useful for culturing cells and includes plates, wells, flasks, multi-well plates, multi-layer flasks, perfusion systems which provide an environment for cell culture.

In embodiments, a "well" is an individual cell culture environment provided in a multi-well plate format. In embodiments, a well can be a well of a 4 well plate, a 5 well plate, a 6 well plate, a 12 well plate, a 24 well plate, a 96 well plate, a 1536 well plate, or any other multi-well place configuration.

As used herein chamber or wells "structured to constrain cells of interest to grow in 3D conformation" or the like means wells having dimensions or treatments, or a combination of dimensions and treatments, which encourage cells in culture to grow in 3D or spheroid conformation rather than as two dimensional sheets of cells. Treatments include treatment with low binding solutions, treatments to render the surface less hydrophobic, or treatments for sterilization, for example.

As used herein "structured to provide" or "configured to provide" means that the article has features that provide the described result.

In embodiments a single "spheroid well" can be a well of a multi-well plate structured to constrain cells of interest to grow as a single 3D cell mass, or as a single spheroid, in that single spheroid well. For example, a well of a 96 well plate (wells of traditional 96 well plates are approximately 10.67 mm deep, have a top aperture of approximately 6.86 mm and a well bottom diameter of approximately 6.35 mm.

In embodiments, "spheroid plate" means a multi-well plate having an array of single-spheroid wells.

In embodiments, a well may have an array of "microcavities." In embodiments, the "microcavity" can be, for example, a microwell that defines an upper aperture and a nadir, a center of the upper aperture, and a center axis between the nadir and the center of the upper aperture. In embodiments, the well is rotationally symmetrical about the axis (i.e. the sidewall is cylindrical). Or, in embodiments, the well may be hexagonal as shown in FIG. 1C, or any other geometry. In some embodiments, the upper aperture defines a distances across the upper aperture of from between 250 µm to 1 mm, or any range within those measurements. In some embodiments the distance from the upper aperture to the nadir (the depth "d") is between 200 µm and 900 µm, or between 400 and 600 µm. The array of microcavities may have different geometries, for example, parabolic, hyperbolic, chevron, and cross-section geometries, or combinations thereof.

In embodiments, a "microcavity spheroid plate" means a multi-well plate having an array of wells, each well having an array of microcavities.

In embodiments, "round bottom" of a well or microcavity well can be, for example, a hemisphere, or a portion of a hemisphere, such as a horizontal section or slice of a hemisphere making up the bottom of the well or microcavity.

In embodiments, the term "3D spheroid" or "spheroid" can be, for example, a ball of cells in culture, which are not a flat two-dimensional sheet of cells. The terms "3D spheroid" and "spheroid" are used interchangeably here. In embodiments, the spheroid is comprised of a single cell type or multiple cell types, having a diameter of, for example, from about 100 to about 500 microns, more preferably from about 150 to about 400 microns, even more preferably from about 150 to about 300 microns, and most preferably from about 200 to about 250 microns, including intermediate values and ranges, depending on, for example, the types of cells in the spheroid. Spheroid diameters can be, for example, from about 200 to about 400 microns. The maximum size of a spheroid is generally constrained by diffusion considerations (for a review of spheroids and spheroid vessels see Achilli, T-M, et. al. Expert Opin. Biol. Ther. (2012) 12(10)).

As used herein "tumor cells" means any cell that is isolated from a tumor, derived from a tumor or causes a tumor when injected into an animal, or derived from a cell that causes a tumor when injected into an animal. Tumor cells can be primary tumor cells that are obtained from an animal, including a human, or tumor cells can be cell lines or genetically engineered cells.

As used herein "insert" means a cell culture well that fits into a well of a spheroid plate or a microcavity spheroid plate. The insert has sidewalls and a bottom surface defining a cavity for culturing cells. The bottom surface is porous to allow cells or chemicals to migrate through the porous bottom surface to affect cells of interest growing in a 3D conformation.

As used herein "insert plate" means an insert plate containing an array of inserts structured to fit into an array of wells of a multi-well plate.

As used herein, a "therapeutic agent" means any bioactive material selected fro a desired, and usually beneficial or therapeutic, effect. A therapeutic agent may include, for example and not by way of limitation, low molecular weight therapeutic agents commonly referred to as "drugs", including all class of action, including by not limited to: anti-neoplastics, immuno-suppressants, immune-stimulants, anti-proliferatives, anti-thrombins, anti-platelet, anti-lipid, anti-inflammatory, anti-biotics, angiogenic, anti-angiogenic, vitamins, ACE inhibitors, vasoactive substances, anti-mitotics, metello-proteinase inhibitors, NO donors, estradiols, anti-sclerosing agents, hormons, free radical scavengers, toxins, alkylating agents, alone or in combination. A therapeutic agent may also include, for example and not by way of limitation, biologic agents, including but not limited to: peptides, lipids, protein drugs, protein conjugates drugs, enzymes, oligonucleotides, ribozymes, genetic material, prions, virus, and bacteria.

As used herein, "cell therapeutic" means any cell that may have an effect on another cell. A cell therapeutic may act by contacting a cell of interest, providing an environment that affects a cell of interest, engulfing a cell of interest (phagocytosis), excreting or otherwise providing a chemical that affects a cell of interest, breaking up a 3D cell mass, or otherwise affects a cell of interest.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied.

The present disclosure describes, among other things, methods and labware for assaying therapeutic agents, including immune cells and drugs, and their effects on tumor cells growing in 3D spheroid conformation in culture. The methods allow for, among other uses, the investigation of the effects of a therapeutic agent, such as immune cells or a drug, on tumor cells, and enable the investigation of homing, tumor cytotoxicity, and tumor immune evasion in a single, easy-to-use, high throughput system for more in vivo-like testing. Unlike most current high throughput models for immune cell migration and invasion assays, which utilize tumor cells cultured in 2D, this model enables the 3D tumor spheroid component for more in vivo-like testing.

In various embodiments, an assay method for detecting active migration and cytotoxicity of a therapeutic agent is disclosed. The assay method comprises culturing tumor cells in a cell culture article to form a spheroid, wherein the cell culture article comprises a chamber, e.g. a well, structured to constrain the tumor cells to grow in a 3D spheroid conformation. The assay method further comprises placing an insert comprising a porous membrane into the cell culture article and introducing a therapeutic agent into the insert. The assay method further comprises, after a period of time, detecting active migration of the therapeutic agent from the insert into the cell culture article chamber, and detecting tumor cell lysis. By combining such a cell culture article and insert comprising a porous membrane, a model to study 3D cancer and immune cell interactions in a single high throughput assay is created. Unlike most current high throughput models for immune cell migration and invasion assays, which utilize tumor cells cultured in 2D, this model enables the 3D tumor spheroid component for more in vivo-like testing. Alternative models for high throughput 3D tumor spheroid formation and cytotoxicity assays are not compatible with permeable supports for the migration and invasion component of these assays. Consequently, this model enables the investigation of immune cell and/or drug homing, tumor cytotoxicity, and tumor immune evasion in a single, easy-to-use, high throughput system.

Cells cultured in three dimensions, such as spheroids, can exhibit more in vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. Cells cultured in three dimensions more closely resemble in vivo tissue in terms of cellular communication and the development of extracellular matrices. For example, traditionally, tumoricidal activity and immune evasion have been studied independently by utilizing cells grown in two dimensions (2D), which may not accurately reflect the complexity of a tumor in a 3D system. The barriers immune cells need to overcome in a 3D system, and in-vivo systems are 3D systems, are much greater than those in a 2D system. The immune cells not only need to migrate to the tumor site, but also need to infiltrate a 3D structure in order to attack the target cells. Further, beyond the physical differences between a 2D and a 3D system, it has been shown that phenotypic differences occur when tumor cells are cultured in 3D that allow for higher resistance to cytotoxicity. Tumor cell spheroids thus provide a superior model for cell migration, differentiation, survival, and growth and therefore provide better systems for research related to diagnostics including drug efficacy, pharmacology, and toxicity testing.

Figure 3A:
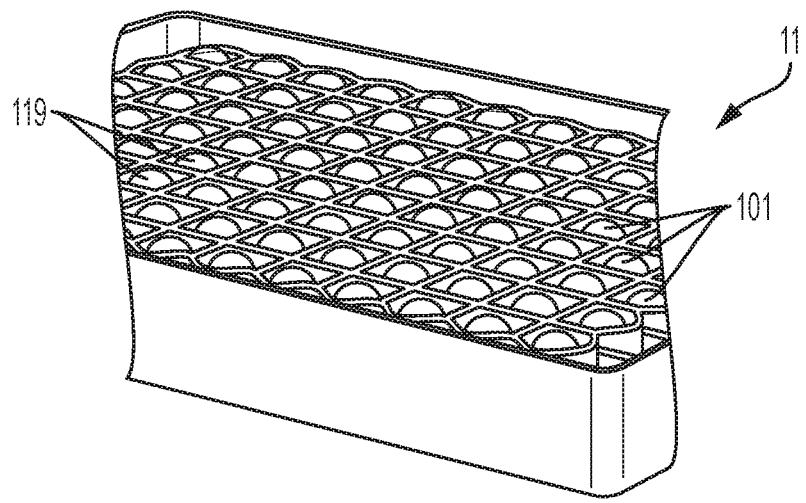
FIG. 3A and FIG. 3B show an embodiment of a spheroid microplate, in this case a 96 well plate, with rounded bottoms configured to contain a single spheroid in each of the 96 wells.
Figure 3B:
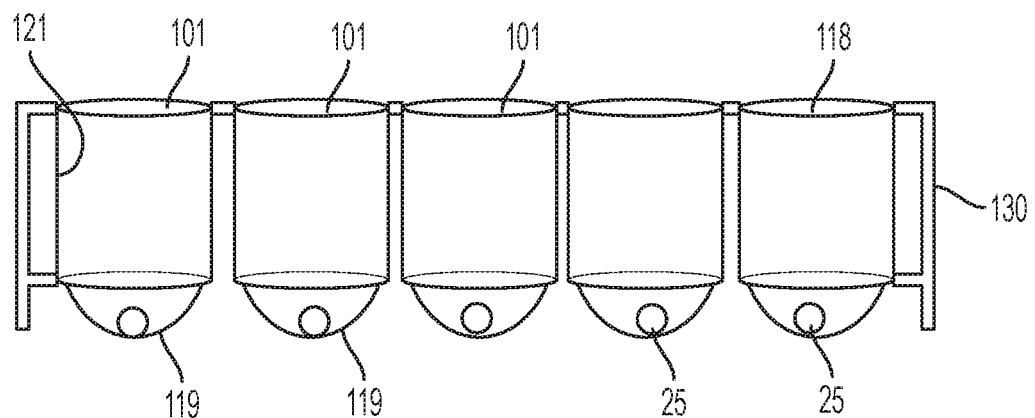

Referring now to FIG. 3A and FIG. 3B, an embodiment of a cell culture article including a chamber structured to constrain the tumor cells to grow in a 3D spheroid conformation, e.g., a spheroid plate, is shown. FIG. 3A shows an embodiment of a spheroid plate 11, in this case a 96 well plate, with rounded bottoms 119 configured to contain a single spheroid in each of the 96 wells. While usually these plates are used with the top aperture 118 of the wells 101 facing up, in FIG. 3A the plate is illustrated upside-down to show the structure of the bottoms of the wells 101. FIG. 3B is an illustration of an embodiment of a spheroid microplate having a frame 130, multiple wells 101, each having a top aperture 118, a side wall 121, and a liquid impermeable, concave arcuate bottom surface 119. 3D tumor cell spheroids 25 are shown at the bottom of each individual well 101. In embodiments the frame 130 may hold the bottom of the wells above a surface such as a lab bench or a table. In some embodiments, there may be an air space provided between the bottom of the wells 119 and the surface underneath the plate. In embodiments, the air space may be in communication with the external environment, or may be closed.

In embodiments, the at least one concave arcuate bottom surface of the chamber can have, for example, a plurality of adjacent concave arcuate bottom surfaces within the same well. Or, as shown in FIG. 1, a multi-well plate may have wells with a flat bottom surface, the flat bottom surface having an array of adjacent concave arcuate bottom surfaces or microcavities within the same well. In embodiments, the cell culture article can be, for example, a single well or multi-well plate configuration having numerous "spheroidal wells", such as a plurality of dimples or pits in the bottom or base of each well, e.g., a microcavity spheroid plate. The plurality of spheroids or spheroid wells per chamber can preferably accommodate, for example, a single or one spheroid per spheroid well.

Figure 1B:
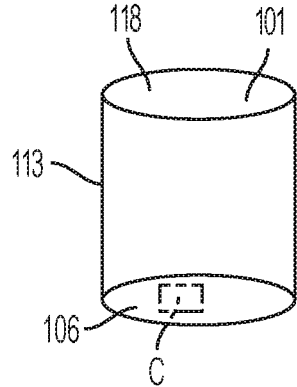
Figure 1C:
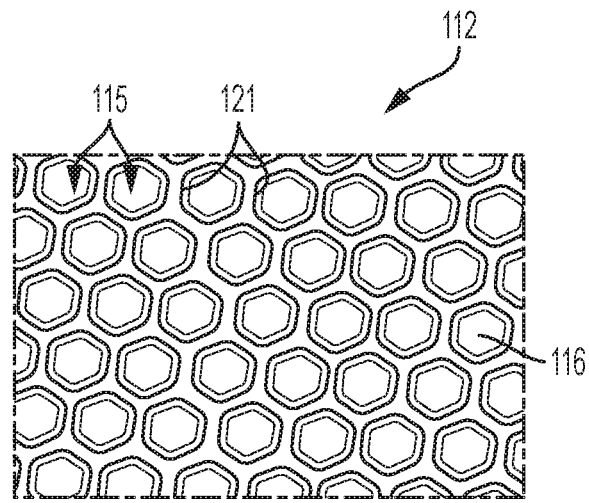

Referring now to FIG. 1A, FIG. 1B and FIG. 1C, an embodiment of a microcavity spheroid plate, in this case a 96-well microcavity spheroid plate, having an array of microcavities on the bottom surface of each well to provide multiple spheroids in each of the 96 wells is shown. FIG. 1A illustrates a multi-well plate 10 having an array of wells 101. FIG. 1B illustrates a single well 101 of the multi-well plate 10 of FIG. 1A. The single well 101 has a top aperture 118, a bottom surface 106, and a sidewall 113. FIG. 1C is an exploded view of the area of the bottom surface 106 of the well 101 shown in the box C in FIG. 1B illustrating an array of microcavities 112 in the bottom surface of the single well shown in FIG. 1B. Each microcavity 115 in the array of microcavities 112 has a sidewall 121 and a bottom surface 116. The microcavity spheroid plate shown in FIG. 1A, FIG. 1B and FIG. 1C, which provides an array of microcavities 112 in the bottom of each individual well 101, can be used to grow a 3D spheroid, in each of the microcavities of each individual well of the multi-well plate. By using this type of vessel, a user can grow a large number of spheroids in each well of a multi-well plate and thereby provide a large number of spheroids that can be treated under the same culture and experimental conditions for use in an assay as provided herein.

Figure 2:
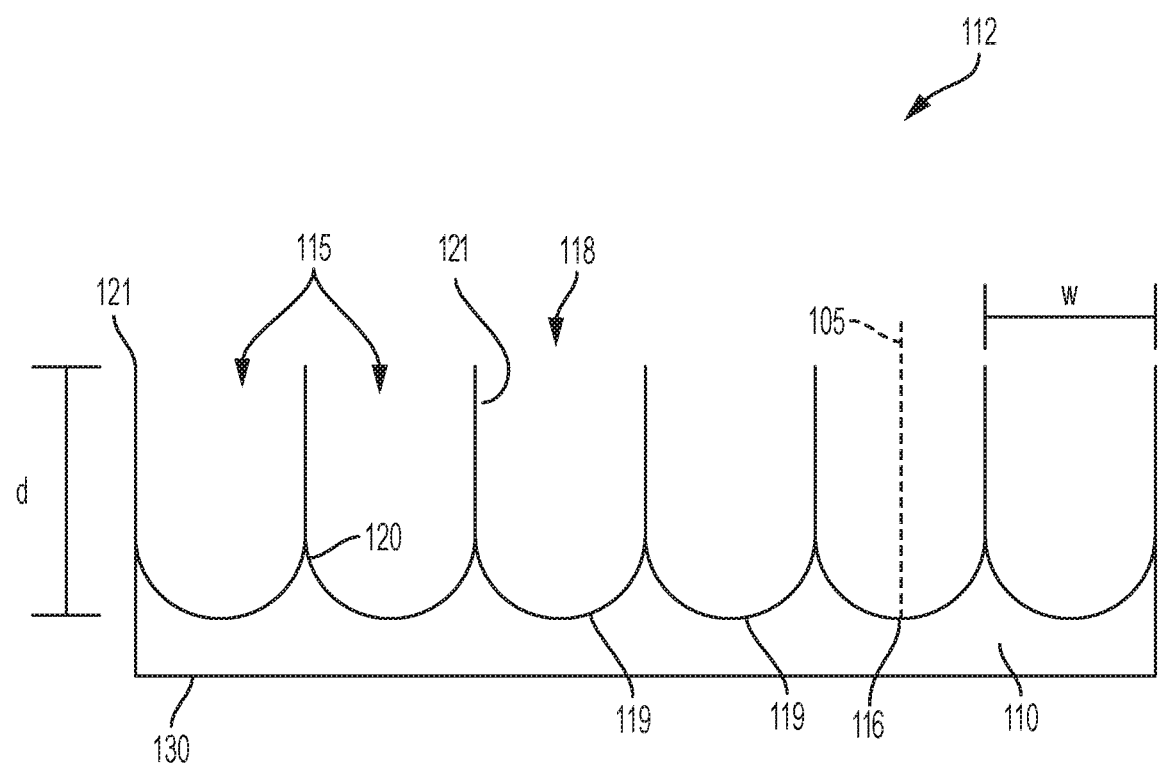
FIG. 2 is an illustration of an array of microcavities.

Referring now to FIG. 2, an illustration of an array of microcavities 112 is shown. FIG. 2 illustrates wells 115, each having top aperture 118, a bottom surface 119, a depth d, and a width w defined by sidewalls 121. As shown in FIG. 2, the array of microcavities have round bottoms 119. In embodiments, the bottom surfaces of the microcavities can be round or conical, angled, flat bottomed, or any shape suitable for forming 3D tumor spheroids. In embodiments, the microcavities have a rounded bottom. The round bottom 119 can have a transition zone 120 as the perpendicular sidewalls transition into a round bottom 119. This can be a smooth or angled transition zone. In embodiments, the "microcavity" can be, for example, a microwell 115 that defines an upper aperture 118 and a nadir 116, a center of the upper aperture, and a center axis 105 between the nadir and the center of the upper aperture. In embodiments, the well is rotationally symmetrical about the axis (i.e. the sidewall is cylindrical). Or, the well may have other geometries such as, for example, a hexagonal shape. In some embodiments, the upper aperture defines a distances across the upper aperture (width w) of from between 250 µm to 1 mm, or any range within those measurements. In some embodiments the distance from the upper aperture to the nadir (the depth "d") is between 200 µm and 900 µm, or between 400 and 600 µm. The array of microcavities may have different geometries, for example, parabolic, hyperbolic, chevron, and cross-section geometries, or combinations thereof. In embodiments, the microcavities may have a protective layer 130 below them to protect them from direct contact with a surface such as a lab bench or a table. In some embodiments, there may be an air space 110 provided between the bottom of the wells 119 and the protective layer. In embodiments, the air space 110 may be in communication with the external environment, or may be closed.

In embodiments, the bottom surface of a chamber having the at least one concave arcuate bottom surface or "cup" can be, for example, a hemi-spherical surface, a conical surface having a rounded bottom, and like surface geometries, or a combination thereof. The chamber (e.g., well) and chamber bottom (e.g. well bottom or microcavity bottom) ultimately terminates, ends, or bottoms-out in a spheroid "friendly" rounded or curved surface, such as a dimple, a pit, and like concave frusto-conicial relief surfaces, or combinations thereof. In embodiments, the at least one concave surface the chamber of the cell culture article includes a hemi-spherical surface, a conical surface having a taper of 30 to about 60 degrees from the side walls to the bottom surface, or a combination thereof. In some embodiments, the at least one concave arcuate bottom surface can be, for example, a portion of a hemisphere, such as a horizontal section or slice of a hemisphere, having a diameter of, for example, from about 250 to about 5,000 microns (i.e., 0.010 to 0.200 inch), including intermediate values and ranges, depending on, for example, the well geometry selected, the number of concave arcuate surfaces within each well, the number of wells in a plate, and like considerations. Other concave arcuate surface can have, for example, parabolic, hyperbolic, chevron, and like cross-section geometries, or combinations thereof.

In embodiments, the cell culture article comprising a chamber, e.g., a spheroid plate or a microcavity spheroid plate, can further comprise a low-adhesion, ultra-low adhesion, or no-adhesion coating on a portion of the chamber, such as on the at least one concave surface and/or one or more sidewalls. Examples of non-adherent material include perfluorinated polymers, olefins, or like polymers, or mixtures thereof. Other examples include agarose, non-ionic hydrogels such as polyacrylamides, or polyethers such as polyethyleneoxide or polyols such as polyvinylalcohol, or like materials, or mixtures thereof.

In embodiments, the side wall surface (i.e., a surround) can be, for example, a vertical cylinder or shaft, a portion of a vertical conic of decreasing diameter from the chamber top to the chamber bottom, a vertical square shaft or vertical oval shaft having a conical transition, i.e., a square or oval at the top of the well, transitioning to a conic, and ending with a bottom having at least one concave arcuate surface, i.e., rounded or curved, or a combination thereof. Other illustrative geometric examples include holey cylinders, holey conic cylinders, first cylinders then conics, and other like geometries, or combinations thereof.

One or more of, for example, a low-attachment substrate, the well curvature in the body and base portions of the cell culture article chambers, and gravity, can induce tumor cells to self-assemble into spheroids. Tumor cells maintain differentiated cell function indicative of a more in vivo-like, response relative to cells grown in a monolayer. In embodiments, the spheroid can be, for example, substantially a sphere, having a diameter of, for example, from about 100 to about 500 microns, more preferably from about 150 to about 400 microns, even more preferably from about 150 to about 300 microns, and most preferably from about 200 to about 250 microns, including intermediate values and ranges, depending on, for example, the types of cells in the spheroid. Spheroid diameters can be, for example, from about 200 to about 400 microns, and the upper diameters being constrained by diffusion considerations In embodiments, the cell culture article can further include opaque sidewalls and/or a gas permeable and liquid impermeable bottom comprising at least one concave surface. In some embodiments, at least a portion of the bottom comprising at least one concave surface is transparent. Well plates having such features can provide several advantages for the instantly-disclosed methods, including removing the need for transferring the tumor cell spheroid from one multiwall plate (in which spheroids are formed and can be visualized) to another plate for conducting assays (e.g., measuring lysis and migration of the therapeutic agent), therefore saving time and avoiding any unnecessary disruption of the spheroid. Further, a gas-permeable bottom (e.g., well-bottoms made from a polymer having a gas permeable properties at a particular given thickness) can allow the tumor spheroid to receive increased oxygenation. An exemplary gas-permeable bottom can be formed from perfluorinated polymers or polymers such as poly 4-methylpentane at certain thicknesses. Representative thickness and ranges of gas permeable polymer can be, for example, from about 0.001 inch to about 0.025 inch, from 0.0015 inch to about 0.03 inch, including intermediate values and ranges (where 1 inch=25,400 microns; 0.000039 inches=1 micron). Additionally or alternatively, other materials having high gas permeability, such as polydimethylsiloxane polymers, can provide sufficient gas diffusion at a thickness, for example, of up to about 1 inch.

In embodiments, the cell culture article can further comprise a chamber annex, chamber extension area, or an auxiliary side chamber, for receiving a pipette tip for aspiration, the chamber annex or chamber extension (e.g., a side pocket) can be, for example, an integral surface adjacent to and in fluid communication with the chamber. The chamber annex can have a second bottom spaced away from the liquid impermeable bottom of the chamber. The chamber annex and the second bottom of the chamber annex can be, for example spaced away from the liquid impermeable bottom of the chamber such as at a higher elevation or relative altitude. The second bottom of the chamber annex deflects fluid dispensed from a pipette away from the liquid impermeable bottom of the chamber to avoid disrupting or disturbing the spheroid.

The assay method for detecting active migration and cytotoxicity of a therapeutic agent further comprises placing an insert comprising a porous membrane into the cell culture article and introducing a therapeutic agent into the insert. In embodiments, an insert comprising a porous membrane can be situated within a portion of the chamber, situated within a portion of the chamber annex, or both the chamber and the chamber annex portion. The insert comprising a porous membrane provides isolation or separation (at least initially) of the therapeutic agent, such as an immune cell or drug, situated in an upper portion of the chamber, in an upper portion of the chamber formed by the porous membrane, or both chambers, from tumor cell spheroid in a lower portion of one or both chambers near the transparent bottom.

Figures 4A, 4B:
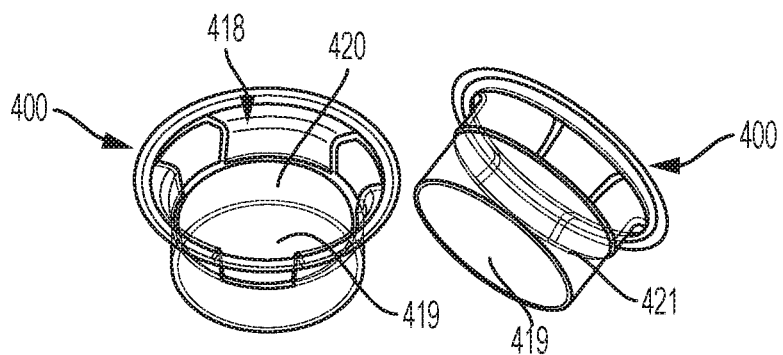
FIGS. 4A and 4B are perspective drawings of an an insert.
Figure 4C:
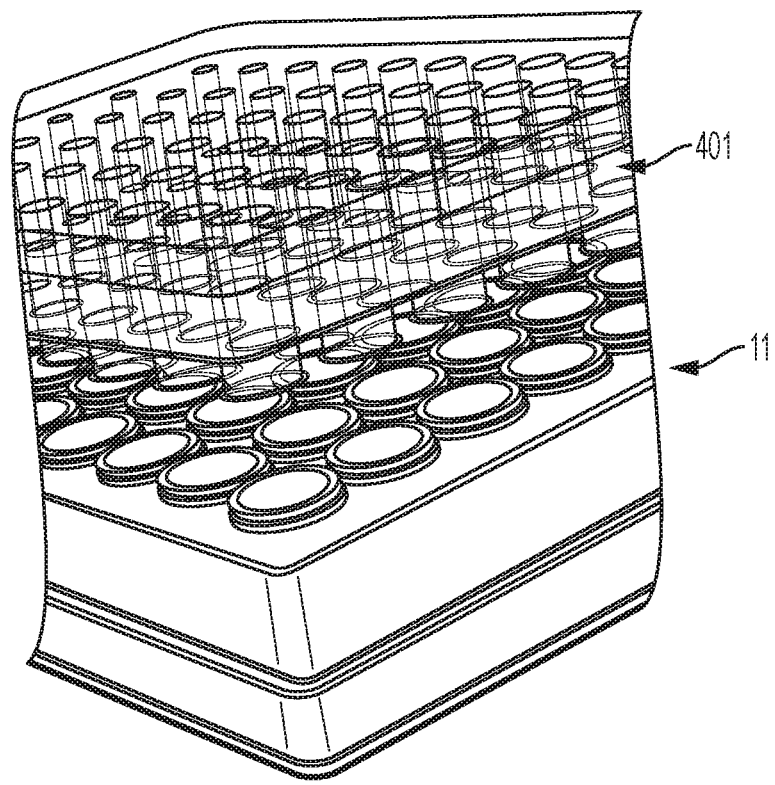
FIG. 4C is a drawing of an insert plate and an associated multi-well plate.

FIG. 4A and FIG. 4B are perspective drawings of an insert 400. The insert 400 shown in FIG. 4A and FIG. 4B is a Corning® Transwell® insert. As shown in FIG. 4A and FIG. 4B, the insert has a top aperture 418, sidewalls 421 and a bottom surface 419 forming a cavity 420. As shown in FIG. 4C, these inserts 400 may be provided in an insert plate 401 configuration where a single plate 401 contains multiple inserts 400 and the multi-well insert plate is structured to insert into the complimentary array of wells in a multi-well plate 11. Inserts are available in many configurations. In embodiments, these inserts have porous bottom surfaces that are sufficiently porous to allow small molecules such as drugs, proteins, vectors, or other materials to pass through the bottom surfaces 119, but not cells. In additional embodiments, inserts have porous bottom surfaces 419 that have pores of sufficient diameter to allow cells, such as cellular therapeutics including immune cells, to migrate through the bottom surface.

The porous membrane of the insert can be made of a variety of different materials, including but not limited to track-etched membrane or a woven or non-woven porous material. The material of the porous membrane may be treated or coated to make it more adherent or more non-adherent to cells or may be treated or coated for any other desirable coating to support cell culture. Treatment may be accomplished by any number of methods known in the art which include plasma discharge, corona discharge, gas plasma discharge, ion bombardment, ionizing radiation, and high intensity UV light. Coatings can be introduced by any suitable method known in the art including printing, spraying, condensation, radiant energy, ionization techniques or dipping. The coatings may then provide either covalent or non-covalent attachment sites. Such sites can be used to attach moieties, such as cell culture components (e.g., proteins that facilitate growth or adhesion). Further, the coatings may also be used to enhance the attachment of cells (e.g., polylysine). Alternatively, cell non-adherent coatings as described above can be used to prevent or inhibit cell binding. The porous membrane may be gamma sterilized. Such inserts are generally available from Corning® (Transwell®) or Millipore® (Millicell® or Ultracell®).

In certain aspects, the porous membrane may be treated or coated so that at least a portion of the porous membrane is configured to simulate a blood-brain barrier (BBB), as is known in the art. In some embodiments, at least a portion of the porous membrane includes an essentially confluent monolayer of endothelial cells, such as but not limited to, microvascular endothelial cells. In some embodiments, the microvascular endothelial cells are brain endothelial cells. In some embodiments, endothelial cells, included microvascular endothelial cells, are used in combination with astrocytes and/or pericytes. Such a model is useful for studying brain cancer, which is the one of the most difficult cancers to treat due to the BBB, which acts as the brain's own defense system. The BBB, which is meant to protect the brain from potential toxins, often prevents conventional therapies, such as chemotherapies, from reaching brain tumors. Traditionally, high throughput testing of compound permeability through the BBB in vitro has been limited to assay of radio- or fluorophore-labeled compounds as they pass a cell monolayer growing on a permeable support system. Unfortunately, the labels themselves may impact the assay, and the ability to determine resulting tumor cytotoxicity must be studied independently. The instantly-disclosed methods and data demonstrate a three dimensional (3D) model to study BBB transport of a therapeutic agent (e.g., a cellular therapeutic, drug, or biologic agent) as well as the resulting brain tumor cytotoxicity of a therapeutic agent, and enable the investigation of homing, tumor cytotoxicity, and tumor immune evasion in a single, easy-to-use, high throughput system for more in vivo-like testing. Unlike most current high throughput models for immune cell migration and invasion assays, which utilize tumor cells cultured in 2D, this model enables the 3D tumor spheroid component for more in vivo-like testing.

In particular aspects of the instantly-disclosed assay method for detecting active migration and cytotoxicity of a therapeutic agent, the disclosure provides the use of Corning® spheroid microplates combined with Corning® 96 HTS Transwells® permeable support systems to provide an environment for carrying out assays. Corning® spheroid microplates are multiple well, cell culture microplates with round well-bottom geometry that are coated with Corning® Ultra-Low Attachment surface, resulting in the ability to form highly reproducible, single multi-cellular tumor spheroids centered in each well. Corning® 96 HTS Transwells® are permeable supports used for high throughput drug transport, and cellular migration and invasion studies.

Figures 5A, 5B, 5C:
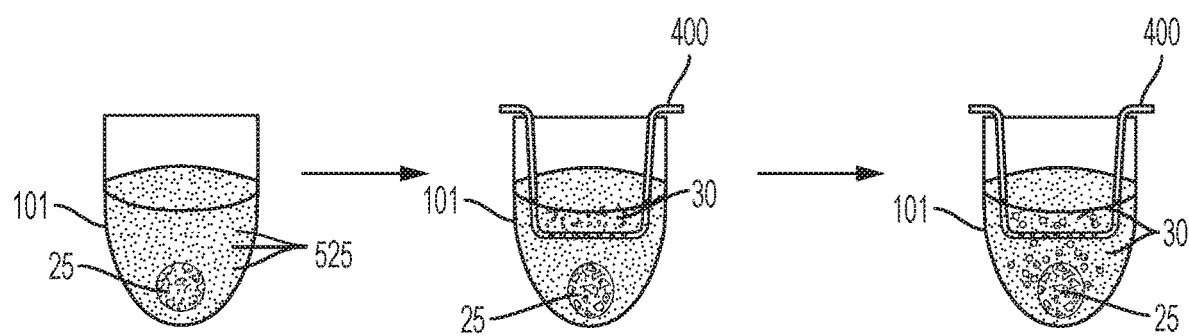
FIGS. 5A, 5B and 5C illustrate an embodiment of the method disclosed herein.

FIGS. 5A-5C illustrate an embodiment of the instantly-disclosed method for detecting active migration and cytotoxicity of a therapeutic agent. As depicted in FIG. 5A, cells of interest 525, such as tumor cells, are grown in media 500 in a well 101 structured to constrain cells of interest 525 to grow in 3D conformation. In this case the well 101 is a single single-spheroid well. In embodiments, the well 101 is, for example, one well of a 96 well plate such as, for example, one well of a Corning® 96 well spheroid plate. In embodiments, cells of interest 525, such as tumor cells could be grown in a well of a multi-well plate (see FIG. 1C) each well 101 having an array of microcavities 112, each microcavity structured to constrain cells of interest to grow in 3D conformation, which would result in the development of an array of spheroids, one in each of the microcavities in the array of microcavities on the bottom surface of a well of a multi-well plate. As the cells grow and multiply in culture, they are constrained to grow as spheroids 25. Over time, a spheroid 25 develops. FIG. 5A illustrates the formation of a spheroid 25. Once the tumor cells develop into a spheroid 25, a cell culture insert 400 is placed into the well 101, as shown in FIG. 5B. In embodiments, the insert may be an insert plate such as that shown in FIG. 4B. A therapeutic agent (e.g., a cellular therapeutic, drug, or biologic agent), in this instance, a cellular therapeutic 30, is added to the cavity 420 of the insert 400. In this configuration, the insert containing the therapeutic agent (e.g., a cellular therapeutic, drug, or biologic agent), such as therapeutic cells 30, and the well 101 containing cells of interest 525 in a 3D conformation, such as 3D tumor spheroids, are incubated together. Then, after a suitable period of time, the effect of the therapeutic agent (e.g., a cellular therapeutic, drug, or biologic agent), in this instance, a cellular therapeutic 30, on the cells of interest, such as the 3D tumor spheroid, as well as the migration of the therapeutic agent from the insert into the assay chamber of the cell culture article, are measured in an assay. This incubation period will vary depending on the type of assay performed, the therapeutic agent, e.g., cellular therapeutic, drug, or biologic agent, which are used in the assay. The incubation period will also vary according to the pore size used for the membrane in the insert 400. Larger pore sizes will lead to a more rapid distribution of the therapeutic agent and thus shorter incubation periods, but might lead to unspecific results. The adjustment of the incubation time can be done in a preliminary experiment and would be well within the general skill of a person skilled in the art. As shown in FIG. 5C, the effects of the therapeutic 30 on the tumor pheroid 25 can then be measured. For example, in FIG. 5C, in embodiments, the assay may measure the dissolution of the spheroid 25.

FIGS. 8A, 8B, 8C, 8D, 8E, 8F and 8G are illustrations of embodiments of the instantly-disclosed method for detecting active migration and cytotoxicity of a therapeutic agent 30 in a model that includes use of a layer of cells 300 on a porous membrane 302 that is part of an insert 400. In these embodiments, the layer of cells 300 on the porous membrane 302 of the insert 400 is configured to simulate a blood-brain barrier (BBB).

First, and as shown in FIG. 8A, cells 300 used to simulate the BBB are seeded onto the porous membrane 302 of cell culture insert 400 in culture media 500. These cells are, for example, endothelial cells. After a period of time, the seeded cells 300, such as endothelial cells, form a confluent monolayer (a 2D layer) of cells 306 which simulates the BBB. Once a confluent monolayer of cells 306 is formed, the insert 400 can be placed into a spheroid well 101, as shown in FIG. 8C.

Similar to FIG. 5, cells of interest, such as tumor cells, are also grown in media 500 in a well 101 structured to constrain cells of interest to grow in 3D conformation and form a spheroid 25, as shown in FIG. 8B. As shown in FIG. 8B, the well 101 is a single single-spheroid well. In embodiments, cells of interest, such as tumor cells could be grown in a well of a multi-well plate having an array of microcavities (as shown in FIGS. 1A, 1B and 1C), each microcavity structured to constrain cells of interest to grow in 3D conformation (see FIG. 1C), which would result in the development of a large number of spheroids, one in each of the microcavities in the array of microcavities on the bottom surface of a well of a multi-well plate. As the cells grow and multiply in culture, they are constrained to grow as spheroids, and a spheroid 25 develops, as shown in FIG. 8B. Once the tumor cells develop into spheroids 25 and the confluent monolayer of endothelial cells 306 which simulates the BBB is formed, the cell culture insert 400 is placed into the well 101, as shown in FIG. 8C.

Still referring to FIG. 8C, and similar to FIG. 5, a therapeutic agent (e.g., a cellular therapeutic, drug, or biologic agent), in this instance, a drug 310, is added to the cavity 312 of the insert 400. In this configuration, the insert 400 containing the therapeutic agent 310 (e.g., a cellular therapeutic, drug, or biologic agent), in this instance a drug 310, and the well containing cells of interest in a 3D conformation, such as 3D tumor spheroids 25, are incubated together. This is shown in FIG. 8D and FIG. 8E. Incubation periods will vary depending on the therapeutic agent, e.g., cellular therapeutic, drug, or biologic agent, which are used in the assay. It will also vary according to the pore size used for the membrane 302 in insert 400. Larger pore sizes will lead to a more rapid distribution of the therapeutic agent 310 and thus shorter incubation periods, but might lead to unspecific results. The adjustment of the incubation time can be done in a preliminary experiment and would be well within the general skill of a person skilled in the art. The use of a layer of cells 306 on a porous membrane 302 that is configured to simulate a blood-brain barrier (BBB) can be used to assess the ability of a therapeutic agent to cross the blood brain barrier.

Then, after a suitable period of time, the effect of the therapeutic agent 310 on the cells of interest, such as the 3D tumor spheroid 25 can be measured. For example, as shown in FIG. 8F, disruption or dissolution of the spheroid 25 is shown. This disruption can be measured by measuring changes in the integrity of the spheroid 25 in the assay chamber 315 of the cell culture article. Or, as shown in FIG. 8G, while the spheroid 25 is shown intact after the incubation period, measurements of cellular function can be made to determine changes in the physiology of the cells making up the spheroid 25. For example, cytotoxic effect of the drug 310 or the infiltration of the drug 310 into the the 3D tumor spheroid 25 can be measured by measuring changes in the tumor cell physiology.

The migration of the therapeutic agent 310 from the insert 400 into the assay chamber 315 of the cell culture article can be measured. For example, a therapeutic agent 310 is introduced into the insert chamber 312 of the device and then an assessment is made with respect to the concentration of drug 310 that is measured from the assay chamber 315 to determine how much drug 310 crosses the blood brain barrier.

Effects on the 3D tumor spheroid and the migration of the therapeutic agent from the insert into the chamber of the cell culture article can be measured by any means known in the art including visualization, fluorescent measurements, genetic, metabolic or protein analysis of the cells, cell extracts, or media. For example, migration of immune cells (where the therapeutic cells are immune cells) and cytotoxicity (or changes in the physiology of the tumor cells) may be assessed, for example but not limited to, by flow cytometry by using appropriate staining as is known in the art and used in the examples herein. Additionally, and by way of example, migration of drugs or biologic agents can be measured by using labeled drugs or biologic agents, including radiolabeled drugs or biologic agents or fluorescently tagged drugs or biologic agents, etc. Infiltration of the therapeutic agent, e.g., a cellular therapeutic, drug, or biologic agent, into the 3D tumor spheroid or tumor cell lysis can be detected, e.g. but not by way of limitation, by visualization and/or fluorescent measurements. For example, the 3D tumor spheroid and infiltrating cells can be fixed and sectioned, and the cells can be stained by conventional histological techniques, as is known in the art.

A wide variety of tumor cell types may be cultured to form the 3D tumor spheroid 25. Cancer cells used for the tumor cell types that may be cultured to form the 3D tumor spheroid 25 include any cells derived from a tumor, neoplasm, cancer, precancer, cell line, or any other source of cells that have the potential to expand and grow to an unlimited degree. Cancer cells are derived from naturally occurring sources or are artificially created. Cancer cells are capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Cancers that serve as sources of tumor cell types that may be cultured to form the 3D tumor spheroid 25 include, but are not limited to, solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, brain cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that serve as sources of cancer cells include, but are not limited to, blood borne cancers such as acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, multiple myeloma, lymphoblastic leukemia, myelogenous leukemia, lymphocytic leukemia, myelocytic leukemia, Hodgkin's disease, non-Hodgkin's lymphoma, Waldenstrom's macroglobulinemia, heavy chain disease, and polycythemia vera. In some embodiments of the methods for detecting active migration and cytotoxicity of a therapeutic agent disclosed herein, the 3D tumor spheroid comprise one or more cancer cells. In some embodiments, the cancer cells are cryopreserved. In some embodiments, one or more of the cells are actively dividing.

In some embodiments, the methods comprise culture media (e.g., comprising nutrients (e.g., proteins, peptides, amino acids), energy (e.g., carbohydrates), essential metals and minerals (e.g., calcium, magnesium, iron, phosphates, sulphates), buffering agents (e.g., phosphates, acetates), indicators for pH change (e.g., phenol red, bromo-cresol purple), selective agents (e.g., chemicals, antimicrobial agents), etc.) as are known in the art.

In some embodiments of the instantly-disclosed method for detecting active migration and cytotoxicity of a therapeutic agent, the therapeutic is a cell therapeutic, drug, and/or biologic agent.

In some embodiments, the cell therapeutic includes an immune cell. In some embodiments, the immune cell is a leukocyte (e.g., a neutrophil, macrophage, dendritic cell, or monocyte). In some embodiments, the immune cell is a lymphocyte (e.g., a natural killer cell, or lymphocyte such as a T cell, B cell, and more particularly cytotoxic T cells).

A wide variety of drugs 310 may be tested in the instantly-disclosed method for detecting active migration and cytotoxicity of a therapeutic agent, including known anti-cancer drugs or substances suspected of potential anti-cancer activity, such as new molecular entities or new chemical entities. Anti-cancer drugs include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalarnycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It should be understood that the instantly-disclosed methods and concepts can be extended to additional co-culture models. For example, while a simulated blood brain barrier has been described, cells grown on the porous membrane can be configured to simulate any biological barrier. A "biological barrier" is a biological membranes that are associated with physiological protective barriers and can include, but are not limited to, a blood-brain barrier, a pulmonary barrier, a placental barrier, an epidermal barrier, ocular barrier, olfactory barrier, a gastroesophageal barrier, a mucous membrane, a blood-urinary barrier, air-tissue barrier, a blood-biliary barrier, oral barrier, anal rectal barrier, vaginal barrier, and urethral barrier. Additional biological barriers include the blood-milk barrier, the blood-testes barrier, and mucosal barriers including the vaginal mucosa, urethral mucosa, anal mucosa, buccal mucosa, sublingual mucosa, rectal mucosa, etc.

Additionally, the cells cultured in the cell culture article to form a spheroid 25 are not limited to tumor or cancer cells. A wide variety of cell types may be cultured. In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown. Cells grown in spheroids may be natural cells or altered cells (e.g., cell comprising one or more non-natural genetic alterations). In some embodiments, the cell is a somatic cell. In some embodiments, the cell is a stem cell or progenitor cell (e.g., embryonic stem cell, induced pluripotent stem cell) in any desired state of differentiation (e.g., pluripotent, multi-potent, fate determined, immortalized, etc.). In some embodiments, the cell is a disease cell or disease model cell. Cells may be from or derived from any desired tissue or organ type, including but not limited to, adrenal, bladder, blood vessel, bone, bone marrow, brain, cartilage, cervical, corneal, endometrial, esophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid. In some embodiments, the cells are mammalian cells (e.g., human, mice, rat, rabbit, dog, cat, cow, pig, chicken, goat, horse, etc.).

Further, the tested effects of the therapeutic agent on the spheroids in the cell culture chamber are not limited to cytotoxicity (e.g., cell lysis). The instant methods and concepts can be applied to drug discovery, characterization, efficacy testing, and toxicity testing. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug interaction assessment, dose assessment, adsorption assessment, disposition assessment, metabolism assessment, elimination studies, etc. As is known to one of skill in the art, specific cells types may be employed for specific tests (e.g., hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity, skeletal myocytes for rhabdomyolysis, etc.). The effects of the therapeutic agent on the spheroid cells may be assessed for any number of desired parameters including, but not limited to, membrane integrity, cellular metabolite content, mitochondrial functions, lysosomal functions, apoptosis, genetic alterations, gene expression differences, and the like.

As such, the instantly disclosed methods and concepts can be used to study, for example and not by way of limitation, the ability of either drug or virus (when the therapeutic agent is a drug or virus) to cross a blood brain barrier or placental barrier (when the porous membrane is configured to simulate a blood brain barrier or placental barrier), and subsequent effect (e.g., cytotoxicity) and infiltration into a tumor spheroid in the cell culture article chamber. Further, and by way of example, the instantly disclosed methods and concepts can be used to study viral infection (when the therapeutic agent is a virus) of the spheroid cells or the effects of a therapeutic agent on embryonic development (e.g., when the spheroid is comprised of embryoin stem cells).

EXAMPLES

The following examples serve to illustrate certain preferred embodiments and aspects of the present disclosure and are not to be construed as limiting the scope thereof.

Example 1

Cell Culture

A549/GFP Cells (Cell Biolabs, Inc. Cat. No. AKR-209), were seeded into 96 well spheroid microplates (Corning Cat. No. 4515) at 2,000 cells per well in Iscove's Modification of DMEM (IMDM) (Corning Cat. No. 10-016-CM) supplemented with 10% fetal bovine serum (FBS) (Corning Cat. No. 35-010-CV). The next day, medium was replaced with 200 of IMDM 10% FBS containing 30 ng/mL of Human SDF-1 alpha (SDF-1α)/CXCL12 (Shenandoah Biotechnology Inc™ Cat. No. 100-20) or vehicle control. NK92-MI cells were stained for one hour with 80 µM CellTracker™ Blue CMHC Dye (Molecular Probes™ Cat. No. C2110) while simultaneously being treated with 2 µg/mL prostaglandin E2 (PGE$_2$) (Tocris Cat. No. 2296) or vehicle control in IMDM without serum for an hour. HTS Transwell-96 Well Permeable Supports were placed in 96 well spheroid plates (a schematic is shown in FIG. 1A and FIG. 4C). NK-92MI cells were then re-suspended in serum free IMDM and seeded into the apical chamber of the inserts at 50,000 cells/insert. After 24 hours, inserts were removed and spheroid microplates were processed for flow cytometry. Briefly, medium was removed and replaced with 150 µL TrypLE™ Select Enzyme (10×) (Gibco™ Cat. No. A1217701) and incubated at 37° C. until spheroids could be broken up into single cells with minimal pipetting. Cells were then analyzed via flow cytometry utilizing the Miltenyi Biotec MacsQuant®.

Evaluation of NK-92MI (NK) Cell Migration

NK-92MI migration and tumoricidal activity of A549/GFP cells was assessed utilizing the commercially available Corning HTS 96 Transwell inserts with the Corning 96 well spheroid microplate, as shown in FIG. 4 and FIG. 5. The presence of certain immune cells in a malignant structure has been shown to correlate with increased patient survival. Unlike more commonly used 2D in vitro models for studying immune cytotoxicity, 3D models can be utilized to observe immune cell infiltration into the tumor spheroid.

Figure 6:
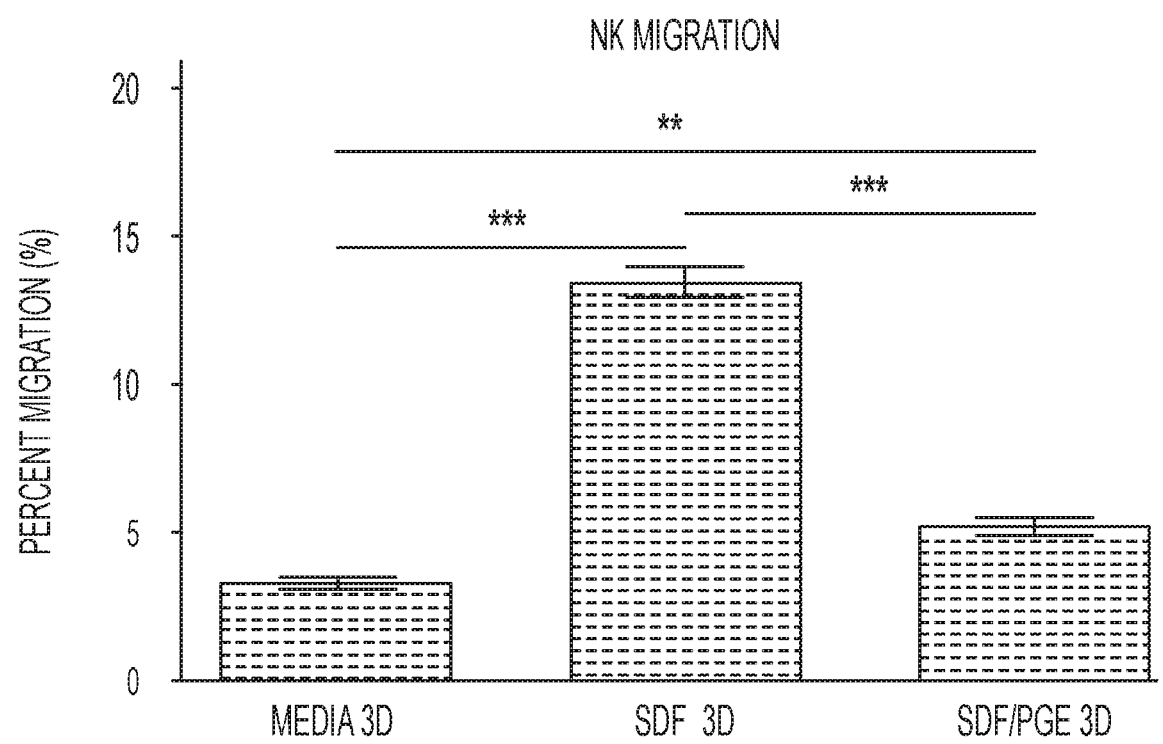
FIG. 6 is a graph showing NK cell migration towards A549/GFP tumor cells cultured in 3D, according to the embodiment illustrated in FIG. 4B.
Figure 7:
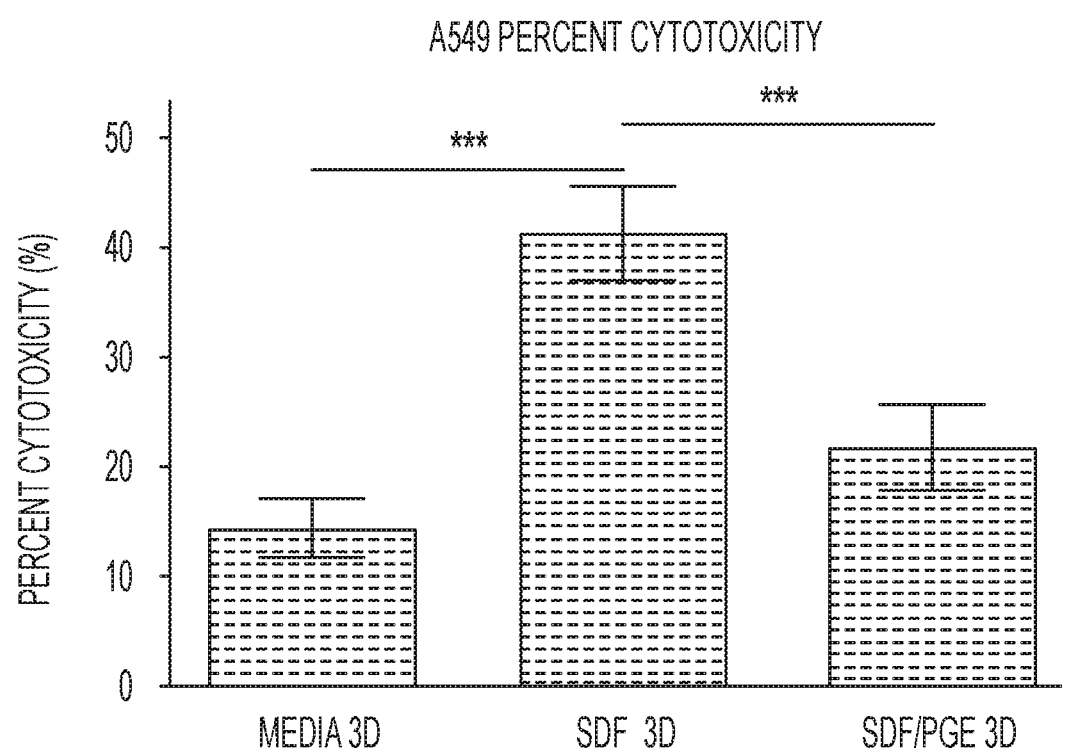
FIG. 7 is a graph showing NK induced cytotoxicity of A549/GFP tumor cells cultured 3D according to the embodiment illustrated in FIG. 4B.

FIG. 6 is a graph showing NK cell migration towards A549/GFP tumor cells cultured in 3D, according to the embodiment illustrated in FIG. 5. Data shown in the average of 2 independent studies, N=24 with 1-way ANOVA with a Bonferroni's post-test. *=$p<0.0001$ and =$p<0.001$. FIG. 6 demonstrates how immune cell migration can be enhanced by the addition of chemokines, such as SDF-1α, as well as suppressed by the addition of inhibitors such as PGE$_2$. NK migration was significantly increased when the chemoattractant SDF-1α was present with the tumor spheroid in the spheroid microplate. FIG. 7 is a graph showing NK induced cytotoxicity of A549/GFP tumor cells cultured 3D according to the embodiment illustrated in FIG. 4A, FIG. 4B, and FIG. 5. Conversely, migration was significantly decreased when NK cells were exposed to PGE$_2$, a known inhibitor of immune cell function often secreted by cancer cells as a form of immune evasion. Tumoricidal activity corresponds well with migration data, with the lowest viability of A549/GFP tumor cells observed with NK cells exposed to SDF-1α without PGE$_2$ (FIG. 7).

Example 2

Blood Brain Barrier Model

Figure 10B:
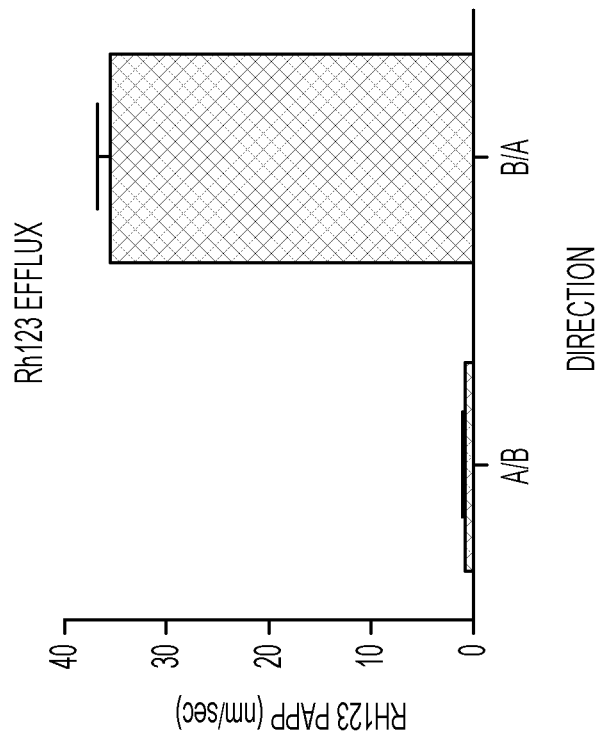
FIG. 10B is a graph showing rhodamine 123 (Rh123) permeability data after 5 days on culture on 96 FITS Transwells in a blood brain barrier (BBB) model. N=120 from 3 independent studies.
Figure 10A:
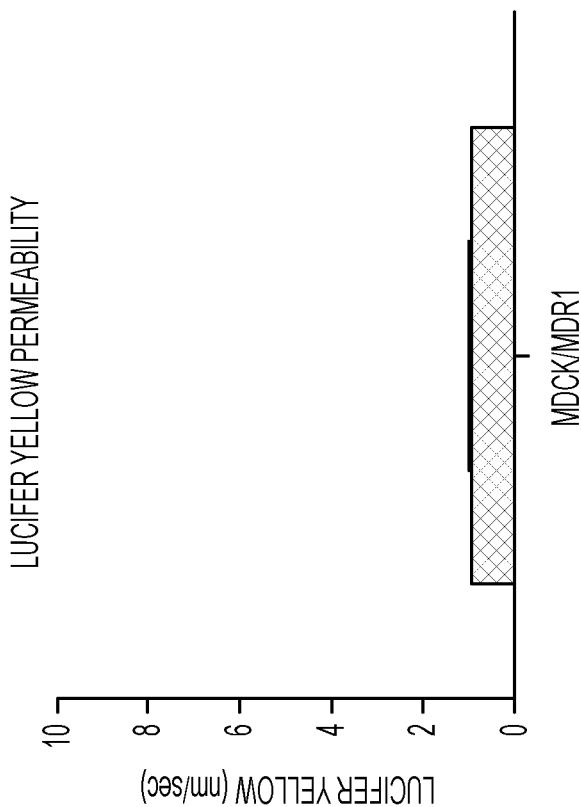
FIG. 10A is a graph showing lucifer yellow permeability.

MDCKII/MDR1 cells were attained from Dr. Piet Borst (Netherlands Cancer Institute, Amsterdam, the Netherlands) and seeded into HTS 96-well Transwells (Corning Cat. No. 3391 or 3977) at 100,000 cells per cm2 in 100 µL of Dulbecco's Modification of Eagle's Medium (DMEM) (Corning Cat. No. 10-013-CM) supplemented with 10% fetal bovine serum (FBS) (Corning Cat. No. 35-010-CV). They were cultured for 5 days with a medium exchange 24 hours prior to assay. Monolayer integrity was assessed via *lucifer* yellow permeability (FIG. 10A) (Sigma Cat. No. L0144) and rhodamine 123 transport (FIG. 10B) (Sigma Cat. No. R8004). Immunostaining of MDCKII/MDR1 monolayers was performed in order to confirm presence of tight junction proteins ZO1 (Thermo Fisher Cat. No. 339188) and occluding (Thermo Fisher Cat. No. 331588) per manufacturer's protocol (data not shown).

Gliomasphere Formation

LN229 cells (ATCC® Cat. No. CRL-2611™) were routinely cultured in DMEM containing 10% FBS. Cells were harvested with Accutase® cell detachment solution (Corning Cat. No. 25-058-CI) and seeded into 96 well spheroid microplates at 1,000 cells per well for 24 hours prior to assay (FIG. 8B).

Blood Brain Barrier/Gliomasphere Model Test

Figure 9:
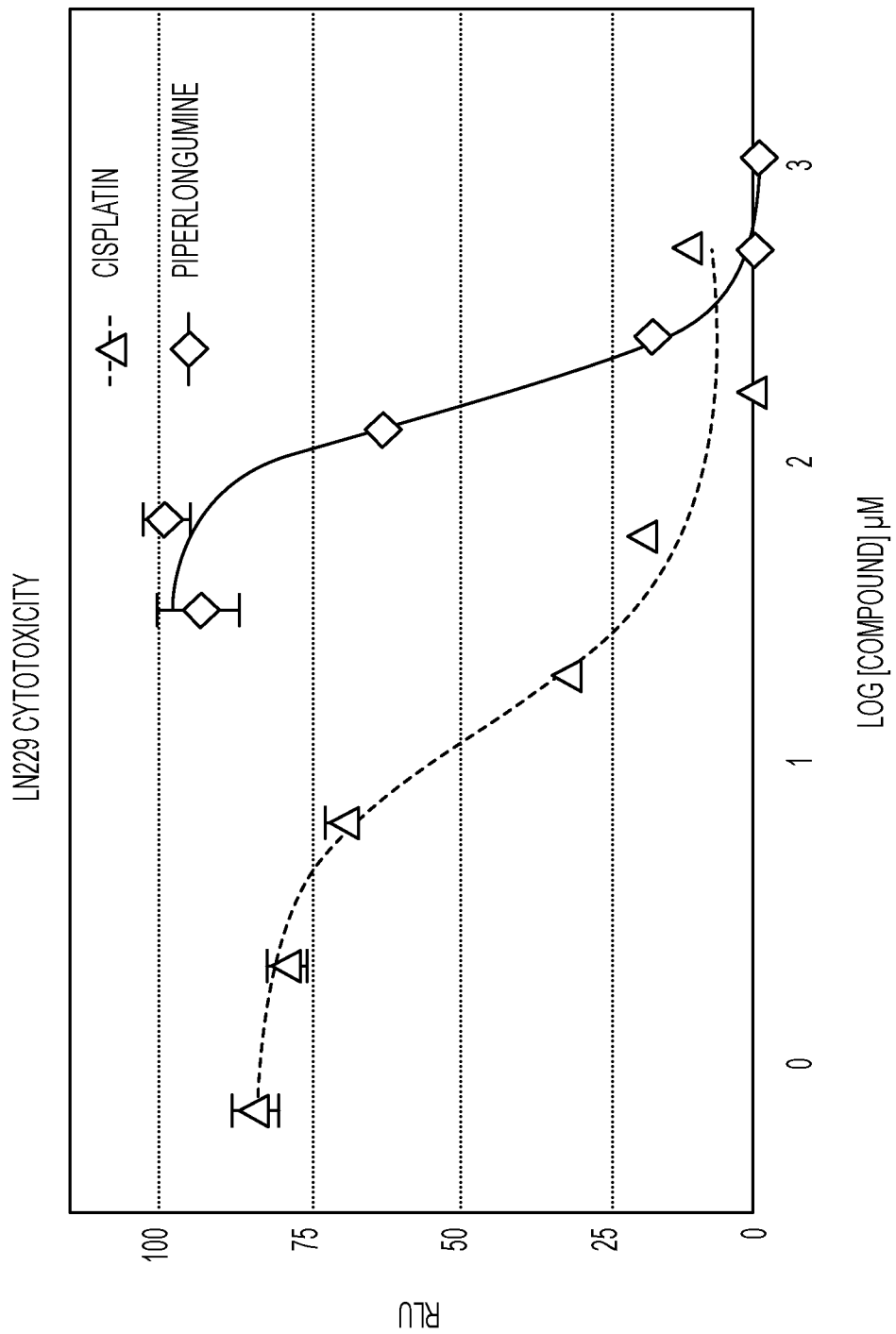
FIG. 9 is a graph showing the dose dependent cytotoxicity of LN229 spheroids after 48 hours of direct culture with compounds Cisplatin and Piperlongumine. N=12 wells per concentration form 2 independent studies.
Figure 11:
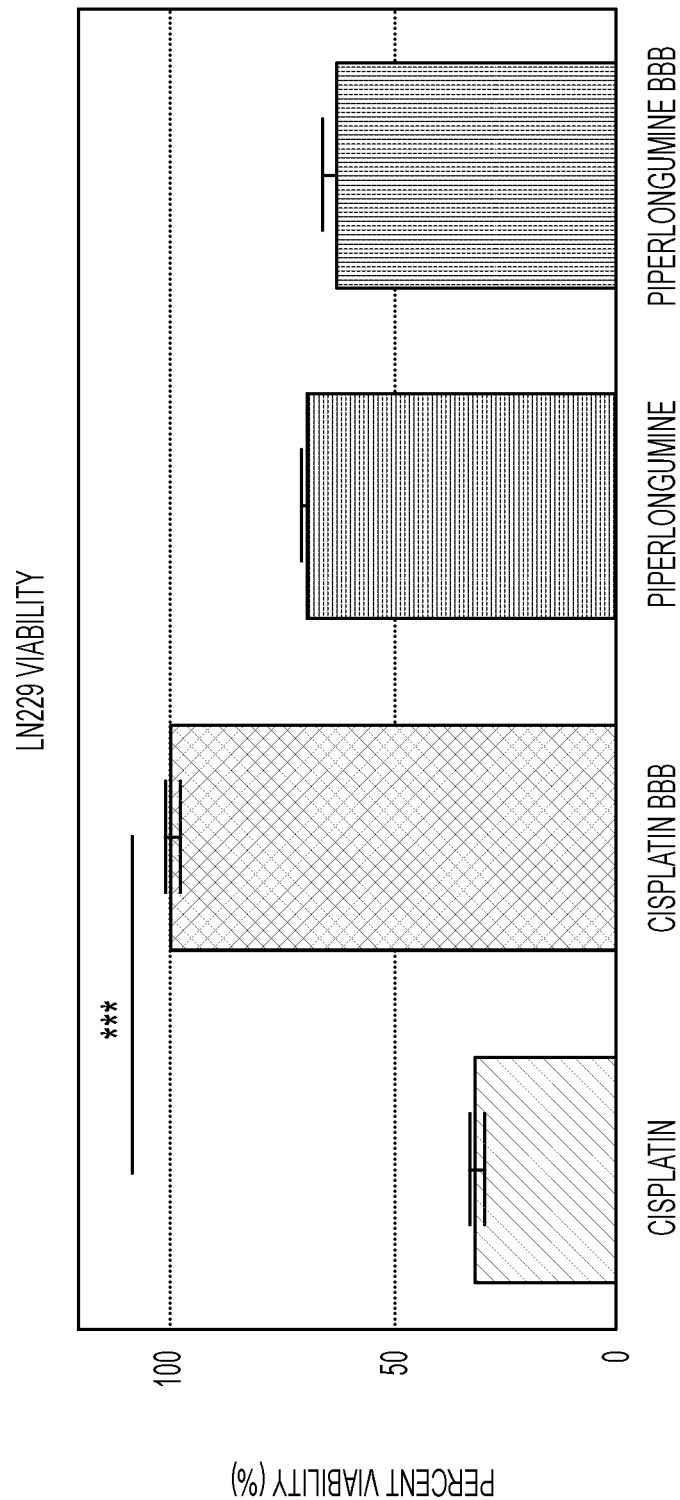
FIG. 11 is a graph showing LN229 cytotoxicity with or without blood brain barrier surrogate. Percent viability of LN229 spheroids 48 hours post 2 hour drug exposure through Transwells with or without a BBB. Viability was assessed by normalizing no drug control to 100% viability. Data shown as the average of 3 independent studies, N=30 with 1-way ANOVA with Boneferroni's post test. ***=$p<0.0001$.
Figure 12B:
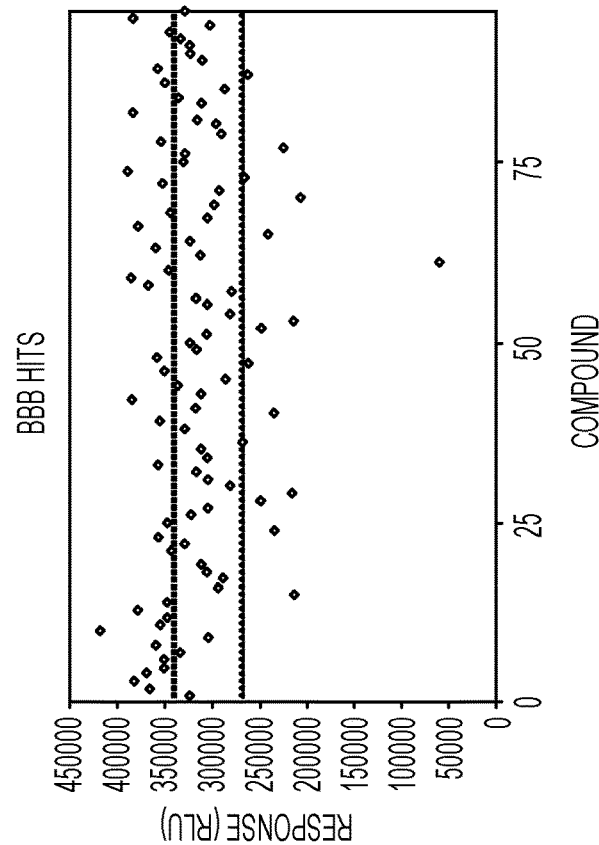
FIG. 12A and FIG. 12B are graphs showing the LN229 Cytotoxicity with or without blood brain barrier surrogate. Percent viability of LN229 spheroids 48 hours post 2 hour drug exposure through Transwells with (FIG. 12B) or without a BBB (FIG. 12A). Viability was assessed by normalizing no drug control to 100% viability. Data shown as the average of 3 independent studies, N=30 with 1-way ANOVA with Boneferroni's post test. ***=$p<0.0001$.
Figure 12A:
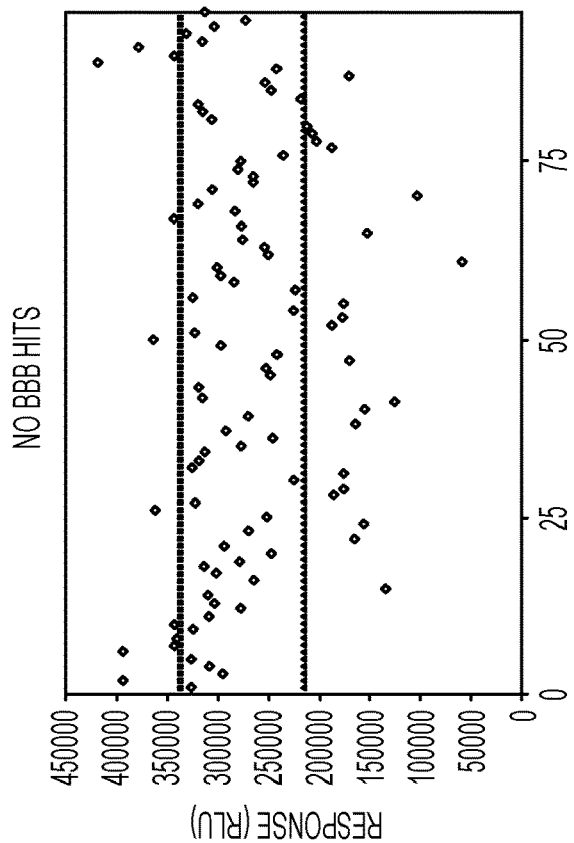

As shown in FIGS. 8A-8G, blood brain barrier/gliomasphere model tests were performed in an embodiment of the instantly-disclosed method for detecting active migration and cytotoxicity of a therapeutic agent in a model that includes use of a porous membrane that is configured to simulate a blood-brain barrier. First and as shown in FIG. 8A, MDCKII/MDR1 cells used to simulate the BBB were seeded onto the porous membrane 302 of cell culture insert 304. LN229 tumor cells were grown in a Corning® 96 well spheroid plates (as shown in FIG. 8B). Once the LN229 tumor cells developed into spheroids (as shown in FIG. 8B) and the confluent monolayer of MDCKII/MDR1 endothelial cells which simulates the BBB on the porous membrane of the cell culture insert (as shown in FIG. 8A) were formed, the cell culture insert was placed into the well. Referring to FIG. 8C, a drug, such as cisplatin or piperlongumine, was added to the cavity of the insert for 2 hours. After drug incubation, the cell culture insert was removed and tested for monolayer integrity (data not shown). Speroids were cultured for 2 additional days (as shown in FIG. 8D and FIG. 8E) and then assayed for tumor cell lysis (as shown in FIG. 8F), e.g., by a stain such as CellTiter-Glo® 3D. Spheroid physiology after treatment (as shown in FIG. 8G) was also tested. FIG. 9 is a graph showing the dose dependent cytotoxicity of LN229 spheroids after 48 hours of direct culture with compounds Cisplatin and Piperlongumine. N=12 wells per concentration form 2 independent studies. FIG. 11 is a graph showing LN229 cytotoxicity of cisplatin or piperlongumine with or without blood brain barrier surrogate. Percent viability of LN229 spheroids 48 hours post 2 hour drug exposure through Transwells with or without a BBB is shown. Viability was assessed by normalizing no drug control to 100% viability. Data shown as the average of 3 independent studies, N=30 with 1-way ANOVA with Boneferroni's post test. ***=$p<0.0001$. FIG. 12A and FIG. 12B are graphs showing a representative screen from Tocris library showing hits found with (FIG. 12B) and without BBB (FIG. 12A). The top dotted line line is average buffer control and the bottom dotted line represents 3 sigma below buffer response. FIGS. 13A and 13B are graphs of the screen summary of FIG. 12A and FIG. 12B showing the compilation of hits discovered with and without a BBB. Hits were considered if they were 3 sigma below buffer response in at least 2 of 3 independent screens. Boxes with a horizontal hatching (besides buffer alone) are hits only found without BBB. Boxes with a diagonal hatching were hits found with and without BBB. As such, the data presented herein demonstrates that the instantly-disclosed methods, which can include the combination of the Corning spheroid microplates and the HTS Transwell 96-well permeable supports, allows for a novel 3D model that can differentiate between compounds that can pass the BBB and those that cannot while also looking at the resulting gliomasphere (or other 3D tumor spheroid) cytotoxicity.

All publications and patents mentioned in the above specification are herein incorporated by reference. It will be apparent to those skilled in the art that various modifications and variations can be made to the present inventive technology without departing from the spirit and scope of the disclosure. Although the disclosure has been described in connection with specific preferred embodiments, it should be understood that the disclosure as claimed should not be unduly limited to such specific embodiments. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An assay method for detecting active migration and cytotoxicity of a therapeutic agent, comprising:
    a) culturing tumor cells in a cell culture article to form a spheroid, wherein the cell culture article comprises a chamber structured to constrain the tumor cells to grow in a 3D spheroid conformation;
    b) placing an insert comprising a porous membrane into the cell culture article and introducing a therapeutic agent into the insert, wherein at least a portion of the porous membrane comprises an essentially confluent monolayer of microvascular endothelial cells and is configured to simulate a blood-brain barrier;
    c) detecting active migration of the therapeutic agent from the insert into the cell culture article chamber;
    d) detecting monolayer integrity after removal of the insert from the cell culture article; and
    e) detecting tumor cell response.

2. The assay method of claim 1, wherein the chamber comprises:
    a side wall;
    a top aperture; and
    a liquid impermeable bottom comprising at least one concave surface, wherein at least a portion of the bottom comprises a low-adhesion or no-adhesion material in or on the at least one concave surface.

3. The assay method of claim 2, wherein the liquid impermeable bottom comprising at least one concave surface is gas-permeable.

4. The assay method of claim 2, wherein the side walls are opaque.

5. The assay method of claim 2, wherein at least a portion of the bottom is transparent.

6. The assay method of claim 2, wherein the at least one concave surfaces comprises a plurality of concave surfaces within the same chamber.

7. The assay method of claim 2, wherein the at least one concave surface comprises a hemi-spherical surface, a conical surface having a taper of 30 to about 60 degrees from the side walls to the bottom surface, or a combination thereof.

8. The assay method of claim 2, wherein the side wall surface comprises a vertical cylinder, a portion of a vertical conic of decreasing diameter form the chamber's top to bottom surface, a vertical square shaft having a conical transition to the at least one concave bottom surface, or a combination thereof.

9. The assay method of claim 2, the article further comprising a chamber annex for receiving a pipette tip for aspiration, the chamber annex comprising a surface adjacent to and in fluid communication with the chamber, the chamber annex having a second bottom spaced away and at an elevation above the bottom surface, wherein the second bottom deflects fluid dispensed from a pipette away from the bottom surface.

10. The assay method of claim 1, wherein the cell culture article comprises from 1 to about 2,000 of said chambers, wherein each chamber is physically separated from any other chamber.

11. The assay method of claim 1, wherein the insert comprises an insert plate.

12. The assay method of claim 1, wherein both active migration of the therapeutic agent and tumor cell response are detected by flow cytometry.

13. The assay method of claim 1, wherein detecting tumor cell response comprises detecting infiltration of the therapeutic agent into the tumor cell spheroid.

14. The assay method of claim 1, wherein detecting tumor cell response comprises measuring tumor cell lysis.

15. The assay method of claim 1, wherein the therapeutic agent is a cell therapeutic.

16. The assay method of claim 15, wherein the cell therapeutic comprises an immune cell.

17. The assay method of claim 16, wherein the immune cell is a leukocyte or a lymphocyte.

18. The assay method of claim 1, wherein the therapeutic agent is a drug.

* * * * *

UNITED STATES PATENT AND TRADEMARK OFFICE
CERTIFICATE OF CORRECTION

PATENT NO. : 10,859,565 B2  
APPLICATION NO. : 15/889766  
DATED : December 8, 2020  
INVENTOR(S) : Hilary A. Sherman Page 1 of 1

It is certified that error appears in the above-identified patent and that said Letters Patent is hereby corrected as shown below:

On the Title Page

On page 2, Column 1, item [56], Line 14, delete "Shperoid" and insert -- Spheroid --, therefor.

On page 2, Column 2, item [56], Line 5, delete "Exaverbate" and insert -- Exacerbate --, therefor.

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*